(12) United States Patent
Yoo et al.

(10) Patent No.: US 7,816,152 B2
(45) Date of Patent: Oct. 19, 2010

(54) IN SITU, EX SITU AND INLINE PROCESS MONITORING, OPTIMIZATION AND FABRICATION

(75) Inventors: Woo Sik Yoo, Palo Alto, CA (US); Kitaek Kang, Dublin, CA (US)

(73) Assignee: WaferMaster, Inc., San Jose, CA (US)

( * ) Notice: Subject to any disclaimer, the term of this patent is extended or adjusted under 35 U.S.C. 154(b) by 764 days.

(21) Appl. No.: 11/734,195

(22) Filed: Apr. 11, 2007

(65) Prior Publication Data
US 2008/0254553 A1    Oct. 16, 2008

(51) Int. Cl.
*H01L 21/00*    (2006.01)
(52) U.S. Cl. .............................. 438/7; 438/10; 324/71.5
(58) Field of Classification Search ............ 438/7, 438/10; 324/71.5
See application file for complete search history.

(56) References Cited

U.S. PATENT DOCUMENTS

| | | | | |
|---|---|---|---|---|
| 6,166,354 A | * | 12/2000 | Hause et al. | 438/14 |
| 6,656,749 B1 | * | 12/2003 | Paton et al. | 438/7 |
| 6,812,045 B1 | * | 11/2004 | Nikoonahad et al. | 438/14 |
| 7,462,324 B2 | * | 12/2008 | Ozaki et al. | 422/82.01 |
| 2007/0026541 A1 | * | 2/2007 | Kokura | 438/7 |

* cited by examiner

*Primary Examiner*—W. David Coleman
*Assistant Examiner*—Sun M Kim
(74) *Attorney, Agent, or Firm*—Haynes and Boone, LLP

(57) ABSTRACT

Methods and systems for in situ process control, monitoring, optimization and fabrication of devices and components on semiconductor and related material substrates includes a light illumination system and electrical probe circuitry. The light illumination system may include a light source and detectors to measure optical properties of the in situ substrate while the electrical probe circuitry causes one or more process steps due to applied levels of voltage or current signals. The electrical probe circuitry may measure changes in electrical properties of the substrate due to the light illumination, the applied voltages and/or currents or other processes. The in situ process may be controlled on the basis of the optical and electrical measurements.

12 Claims, 8 Drawing Sheets

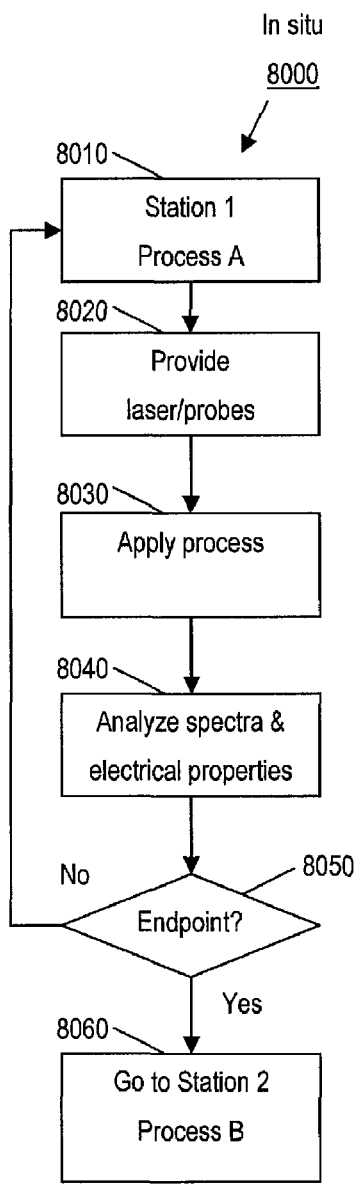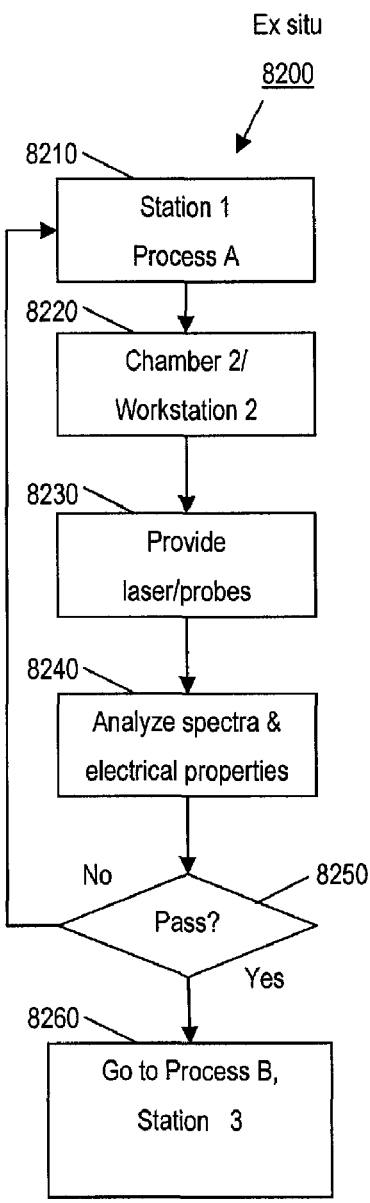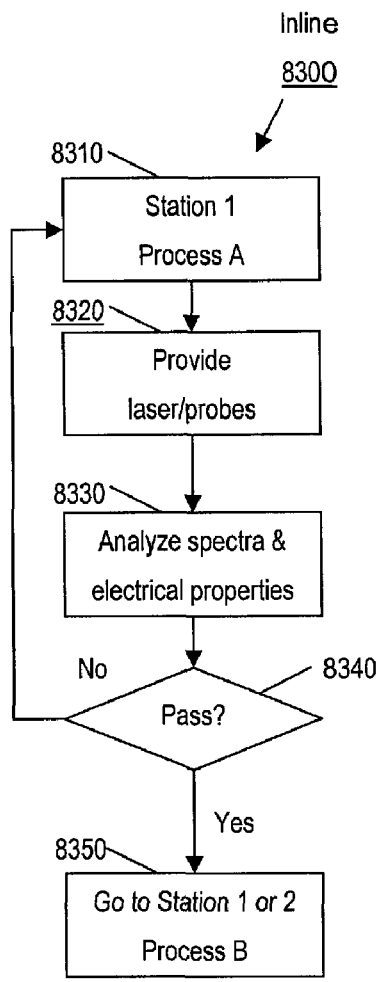
FIG. 8A — In situ 8000
FIG. 8B — Ex situ 8200
FIG. 8C — Inline 8300

IN SITU, EX SITU AND INLINE PROCESS MONITORING, OPTIMIZATION AND FABRICATION

BACKGROUND

1. Field of Invention

This disclosure generally relates to in situ, ex situ and inline methods of process monitoring, optimization and device fabrication methods in semiconductor processes.

2. Related Art

A number of methods exist for monitoring semiconductor processes in situ, ex situ and inline, where low pressure, high temperature, reactive gases, plasma discharge, or other extreme conditions are required for fabrication. One objective may be to optimize the process conditions to produce the highest quality results in the shortest time, with least expenditure of energy or material, i.e., production efficiency. Another objective may be to detect endpoint conditions in a fabrication step, i.e., accuracy and uniformity. For example, secondary ion mass spectrometry (SIMS) may be used for endpoint detection in sputter etching processes. Residual gas analysis (RGA) may be used to control partial pressure in reactive deposition and etch systems. Quartz crystal oscillators may be used to monitor and control deposition thickness. However, all these monitoring, endpoint detection and optimization, and control systems typically require complex equipment and/or vacuum conditions. Therefore, there is a need for simplified means of performing many types of process monitoring and control.

SUMMARY

Methods of in situ, ex situ and inline process monitoring and optimization of semiconductor devices and components are disclosed.

In accordance with an embodiment of the disclosure, a method of in situ monitoring and control includes a first chamber, a substrate, on which devices are to be fabricated and which are configured with electrical contact pads at selected locations. The substrate is provided on a stage adapted to position and orient the substrate, position and orient electrical probes configured as part of an electrical sensing circuit, or a combination of both. The probes contact selected contact pads and monitor voltage drop, resistance, and/or current between the pads during a fabrication process. The substrate may be selectively exposed to light beams of selected wavelength, power density and modulation. The light beam may be a laser or other suitable light source, and may be applied to perform monitoring and diagnostic tasks or may be applied to perform process fabrication steps. Alternatively, the light beam may be used to simultaneously perform monitoring/diagnostics/control and process fabrication. Electrical measurements via the contact pads may be made during the application of light to monitor and optimize the fabrication process.

The obtained data may be used to control process parameters for a desired result and/or detect a defined endpoint condition for terminating the process. Alternatively, current densities or voltages may be applied via the contact pads to perform fabrication steps that are monitored and optimized both electrically and optically. Alternatively, both monitoring and process fabrications steps may be performed simultaneously using the disclosed electrical methods. In another embodiment, monitoring and process evaluation may be performed in a second chamber or workstation different from the first chamber, following process steps performed in the first chamber. Alternatively, monitoring and process evaluation may be performed inline in the same chamber, between a first process step and a second process step.

In accordance with another embodiment of the disclosure, in situ direct fabrication is performed on a substrate on which devices are to be fabricated, and configured with electrical contact pads at selected locations. The substrate is provided on a stage adapted to position and orient the substrate, position and orient electrical probes configured as part of an electrical circuit, or a combination of both. The probes contact selected contact pads and provide voltage, and/or current sources to the pads to maintain a selected electrical condition in the region affected by the contacted pads during a fabrication process. The electrical condition may be used to control and produce a desired fabrication result. The fabrication process may be monitored and controlled by illuminating the substrate with a light source of selected properties, i.e., wavelength, power, modulation, etc., to obtain information optically about the processed regions of the substrate. The method of optical illumination may simultaneously comprise a process and provide process parameters measurement for achieving a desired process result and/or detect a defined endpoint condition for terminating the process. In one embodiment, monitoring and process evaluation may be performed in a second chamber or workstation different from the first chamber, following process steps performed in the first chamber. Alternatively, monitoring and process evaluation may be performed inline in the same chamber, between a first process step and a second process step.

BRIEF DESCRIPTION OF THE DRAWINGS

FIG. 8A is a diagram of methods of in situ process monitoring according to various embodiments.

FIG. 8B is a diagram of methods of ex situ process monitoring according to various embodiments.

FIG. 8C is a diagram of methods of inline process monitoring according to various embodiments.

Like reference symbols in the various drawings indicate like elements.

DETAILED DESCRIPTION

Figure 1:
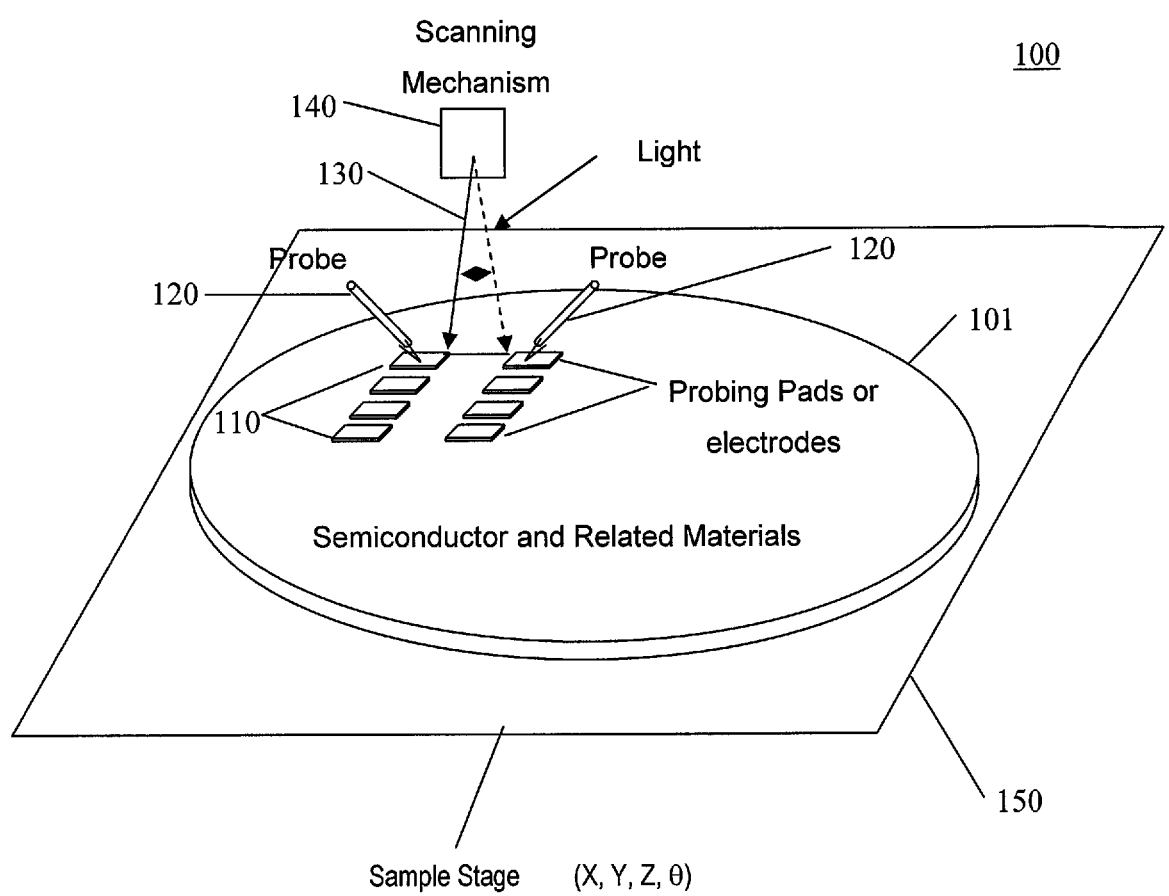
FIG. 1 illustrates an apparatus for in situ process monitoring, control, and fabrication, in accordance with an embodiment of the disclosure.

FIG. 1 illustrates a system 100 of process monitoring, control, and fabrication, in accordance with an embodiment of the disclosure. A semiconductor or related material substrate 101 is disposed on a sample stage 150. Sample stage 150 may be configured to position and orient substrate 101 by X, Y, Z translation and θ rotational orientation. One or more light beams 130 may be provided to illuminate substrate 101 with a scanning mechanism 140. Z translation provides motion to enable a change of position of substrate 101 relative to any focusing optics included in a scanning mechanism 140, so that light beam 130 may be brought to a focus above, at or below the surface of substrate 101. Alternatively, focusing optics that may be incorporated in scanning mechanism 140 may be substantially translatable in the Z direction by means of piezo-motor or other well known mechanical translation stages. Therefore, various aspects of process monitoring, control and fabrication may be accomplished on the surface of substrate 101 or as varying depths below the surface. Scanning mechanism 140 may be configured to provide the beam as a collimated beam, a spot focused beam, to illuminate substrate 101 in a scanned or other selected pattern, and may be configured to vary the spot size and/or focus above, at or below the surface of the substrate. Scanning mechanism 140 may be any suitable conventional mechanism for positioning and/or moving a light beam.

Substrate 101 may have a plurality of electrode pads 110 selectively disposed on the surface configured for a plurality of electrical probes 120 to make contact therein. Electrical contact may also be made to substrate 101 via stage 150. Contact probes 120 may be configured to make contact with selected electrode pads 110 for measuring electrical resistance, and/or applying selected voltages and/or currents. Contact probes 120 may also include stage 150 as a contact probe (not shown) to make measurements via the back surface of substrate 101.

Contact pads 110 may be formed by depositing conductive materials on substrate 101 and patterning the pads using photolithographic techniques or, alternatively by direct deposition through a mask. Contact pads may also be formed by selective optical illumination using light beam 130 and scanning mechanism 140, wherein the light intensity may produce annealing, ohmic contact or other effects to enable probes 120 to make electrical contact with substrate 101.

Light beam 130 and electrical contact pads 110 may be used to provide monitoring, optimization and fabrication processes in a combination of ways. Light beam 130 may be selected to have properties that result in processes that change selected portions of substrate 101 in desired ways. For example, light beam 130, appropriately selected, may be used to form exposed patterns of photo resist for subsequent process steps or, in a later step, to ash and remove resist after a developing and/or etching process takes place. Light beam 130 may be used to excite a chemical reaction near the surface of substrate 101 in the presence of liquid or vapor phase chemical to produce direct deposition at selected, e.g., scanned, regions of substrate 101. Light beam 130 may be focused to produce light densities at or below the surface of substrate 101 to produce annealing, activation, epitaxial interlayer dislocation stress reduction, and the like. Light beam 130 may be a laser beam, may be a continuous beam, pulsed or modulated, and may be selected to have, for example, a specific wavelength, a spectral range of wavelengths, or a plurality of specific wavelengths.

Figure 2A:
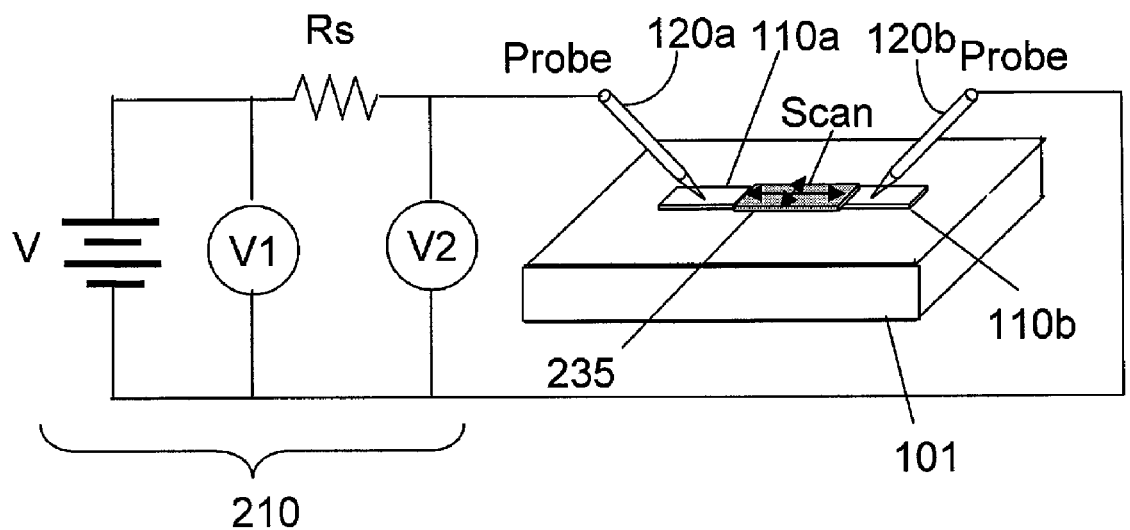
FIGS. 2A and 2B illustrate an apparatus for in situ electrical monitoring of an optically induced process, in accordance with an embodiment of the disclosure.
Figure 2B:
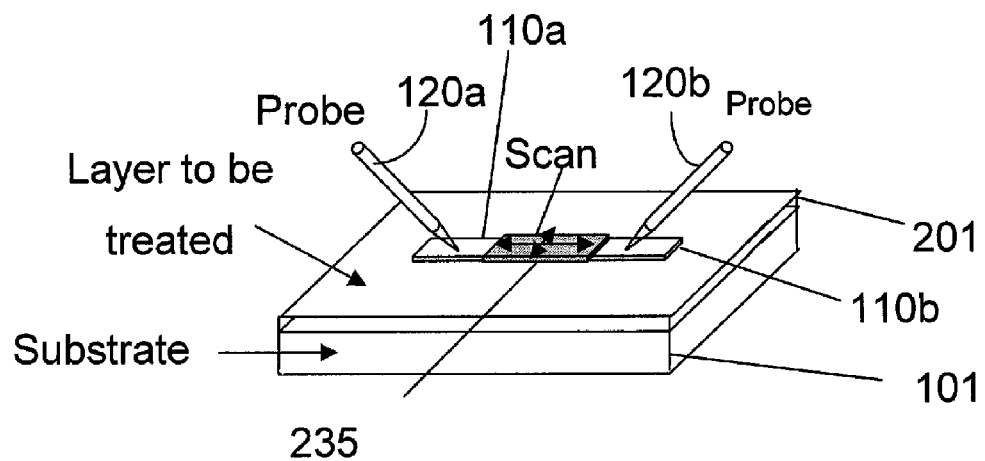

FIGS. 2A and 2B illustrate a portion of substrate 101 which is electrically monitored for an optically induced process, in accordance with an embodiment of the disclosure. An electrical circuit 210 includes a voltage source V, which may be constant, a volt meter V1 in parallel with and measuring voltage source V, a resistor Rs with one side connected to one terminal of voltage source V and meter V1, a second volt meter V2 connected between the second terminal of Rs and the second terminals of voltage source V and meter V1. The connected terminals of resistor Rs and volt meter V2 are connected to a first probe 120a, which is in contact with a first electrode pad 110a, while the second terminals of voltage source V, volt meter V1 and volt meter V2 are collectively connected to a second probe 120b in contact with a second electrode pad 110b. Scanning mechanism 140 may direct light beam 130 to scan a selected area 235 between first electrode pad 110a and second electrode pad 110b. Volt meter V2 monitors the voltage difference between electrode pads 110a and 110b. Light beam 130 may be intense enough to produce annealing in a surface layer 201 (FIG. 2B) of the scanned region of substrate 101, and thereby change electrical resistance in a channel drawn between electrodes 110a and 110b.

Figure 2C:
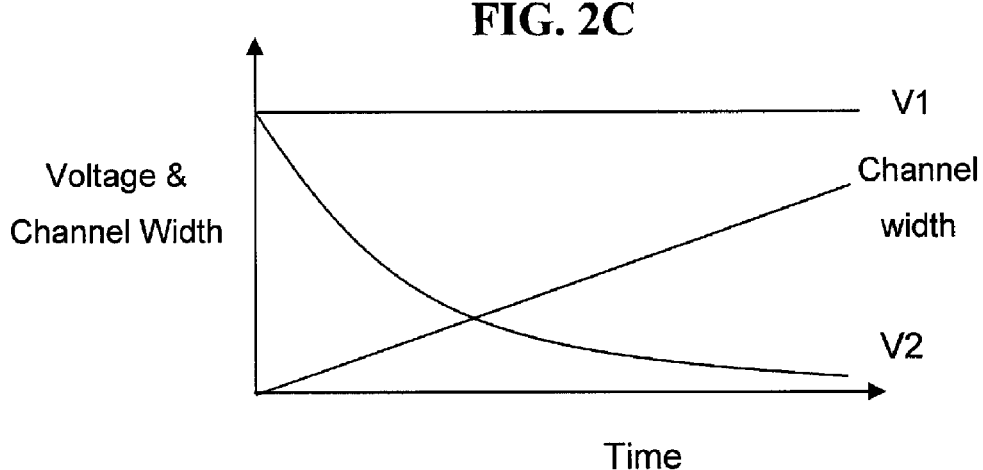
FIG. 2C illustrates the expected behavior of a measurement circuit used for in situ process monitoring, control, and fabrication, in accordance with an embodiment of the disclosure.

FIG. 2C is illustrative of a voltage difference measured between electrode pads 110a and 110b as light beam 130 is scanned between them to produce a channel of selected depth and increasing width. As the width of the annealed layer of the scanned region increases, the resistance of the scanned region may decrease according to the relationship $$Rc = Rs\left(\frac{V2}{V1-V2}\right) \quad (1)$$

where Rc is the channel resistance, which decreases over time as the of the voltage measured by volt meter V2 decreases, as shown in FIG. 2C. V1 and V2 are the voltages measured by the first and second volt meters, respectively. This technique may also be applied to monitor implant activation by laser irradiation, optically induced changes in leakage current, charge mobility, carrier lifetime. For example, minority carrier lifetime response measurement can be accomplished by applying discrete short pulses of light and measuring the time dependent conductivity response. Additionally, electrical probe monitoring and process control may be applied during other fabrication processes besides light beam based processing, such as plasma or sputter deposition or etching.

Figure 2D:
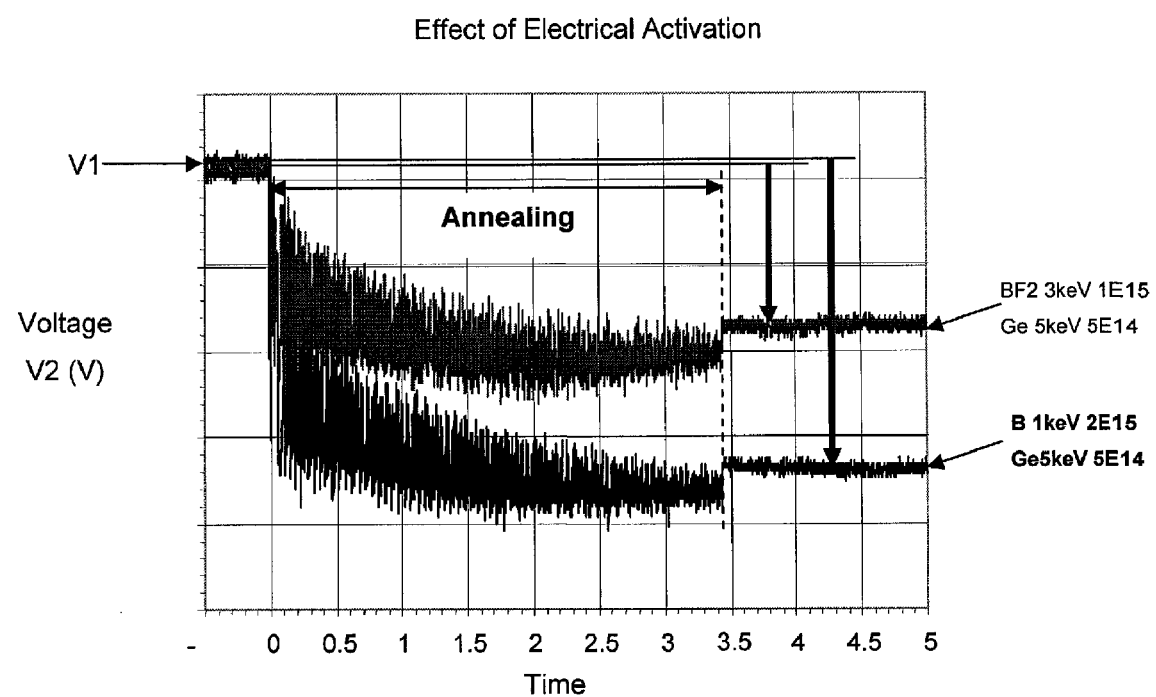
FIG. 2D shows representative results of a measurement circuit used for in situ process monitoring, control, and fabrication, in accordance with an embodiment of the disclosure.

FIG. 2D presents two examples of data obtained during in situ monitoring of a laser annealing process. In these examples, Rs is 100 ohms, and the source voltage V1 was 6.1 volts. While laser beam 130 scans area 235 between two electrode pads 110a and 110b, the monitoring circuit measures the voltage drop V2 between the two pads. As discussed above, measuring V2 determines the resistance between electrode pads 110a and 110b. Referring to FIG. 2D, laser annealing takes place from time T=0 to 3.5 seconds. Each case corresponds to different conditions of prior ion implantation. Before annealing begins, both samples register a value for V2 of approximately 6.1 volts, which, according to equation (1) indicates that the resistance is extremely high (i.e., essentially open circuit). After annealing, one sample voltage V2 is approximately 5.1 volts, and the second sample voltage V2 is approximately 4.3 volts. Referring to equation (1), computed resistance values of the two respective samples of 510 ohms and 239 ohms are obtained. This process may be carried out in situe or ex situ to determine the degree of electrical activation. By conducting the measurement as a monitor during the annealing process, the degree of electrical activation, in terms of path resistance, may be accurately controlled.

Figure 3:
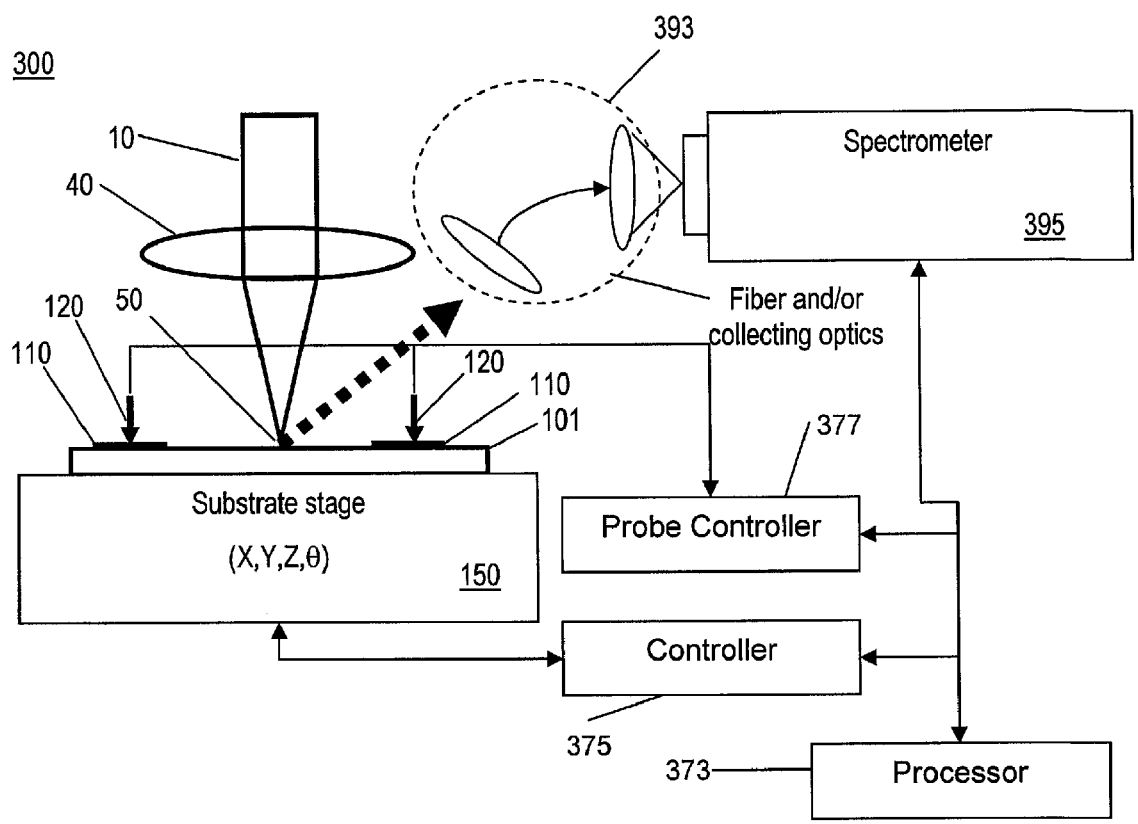
FIG. 3 shows a representative system for optical and electrical in situ process monitoring, control, and fabrication, in accordance with an embodiment of the disclosure.

FIG. 3 illustrates an apparatus 300 including electrical contacts and laser optical spectroscopy to simultaneously monitor and control a process wherein the method is both a process driver and a means of monitoring the process. For example, a laser beam 10, which is focused to a spot 50 by optical components 40 at substrate 101, may be used to perform a fabrication process, such as, for example, resist ashing and removal, thermal annealing and/or activation, ablation, subsurface implant activation, optically excited chemical vapor deposition, or numerous other processes. Simultaneously, the laser induced process may generate optical emission, which is collected by collecting optics 393 and input to a spectrometer 395. Further details can be found in commonly-owned U.S. patent application Ser. No. 11/689,419, incorporated by reference in its entirety. Additionally, probes 120 in contact with electrodes 110 on substrate 101 may monitor conductivity as an indicator of electrical properties on substrate 101 as the fabrication process proceeds. Voltages and currents may also be applied through probes 120 to electrodes 110 by a probe controller 377 to produce bias, heating or charge density effects in substrate 101 that also produce desired process effects.

Substrate stage 150, probe controller 377, a system controller 375, spectrometer 395, and a laser system (not shown) providing laser beam 10 may all be under the control of a processor 373. Therefore, it can be seen that process monitors can also be adapted to provide fabrication processes. Additionally, other processes, such as sputter deposition, ion milling, ion implantation, evaporation, chemical vapor deposition (induced by methods other than with lasers), etc., may be deployed in conjunction with the above example of process control and fabrication. Furthermore, other forms of optical sensing may be employed to monitor and control processes. These may include Raman spectroscopy, ellipsometry, diffractometry, reflectometry, refractometry, scattering and other optical measurement and spectroscopy methods known in the art.

Figure 4:
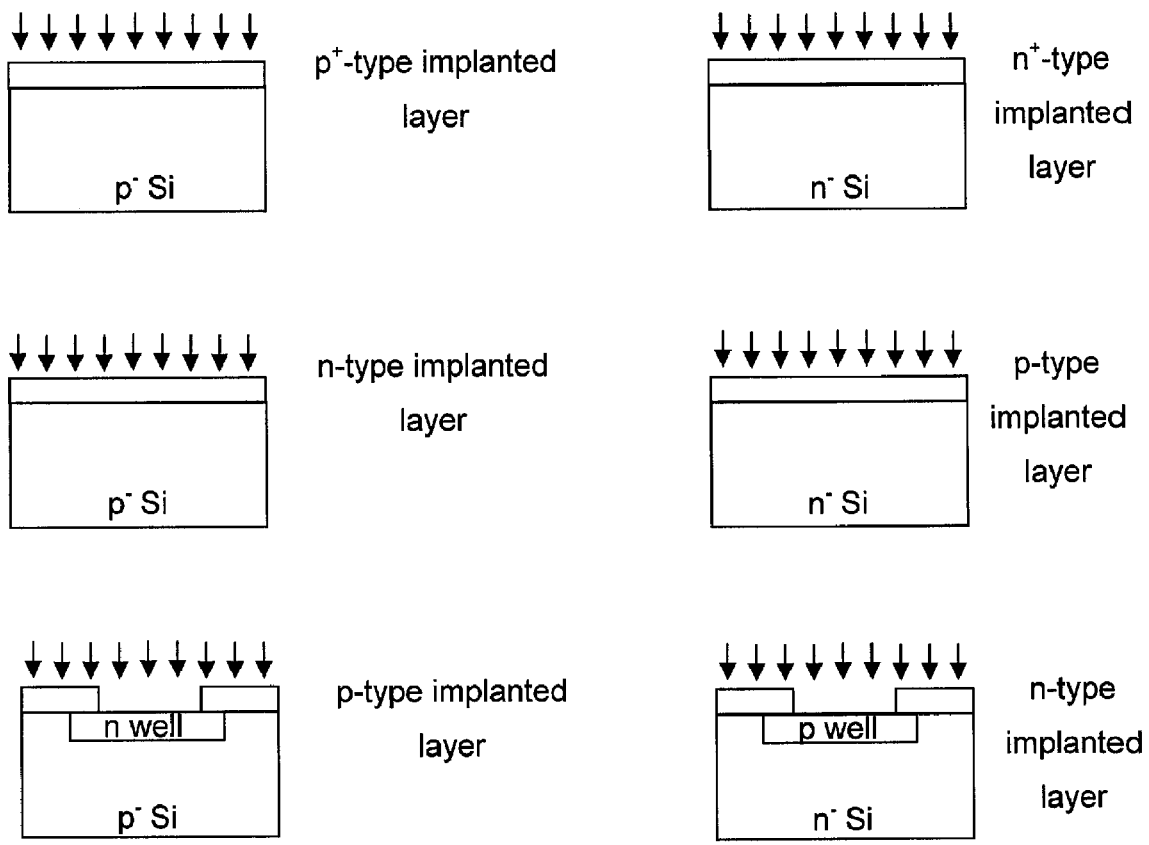
FIG. 4 illustrates six configurations of ion implant activation monitoring, in accordance with an embodiment of the disclosure.

FIG. 4 illustrates six examples of ion implant activation monitoring, in accordance with an embodiment of the disclosure. In these examples, where blank substrates are implanted, a four point probe (not shown) may be used as an equivalent substitute of electrode pads 110 to measure sheet resistivity while light beam 130 is used to induce ion activation. For a patterned substrate, portions such as annealed contact areas, quantum well regions, etc., may be used as contact probe points. Measurements may be made, for example, by measuring resistivity/conductivity as a function of illumination by light beam 130, which may be a scanned or stationary focused beam or a broader area source. This measurement may be performed during implant activation to control and optimize the procedure. Alternatively, as described with reference to FIGS. 2A-2D, laser scanning may be provided after implantation to control activation.

Figure 5:
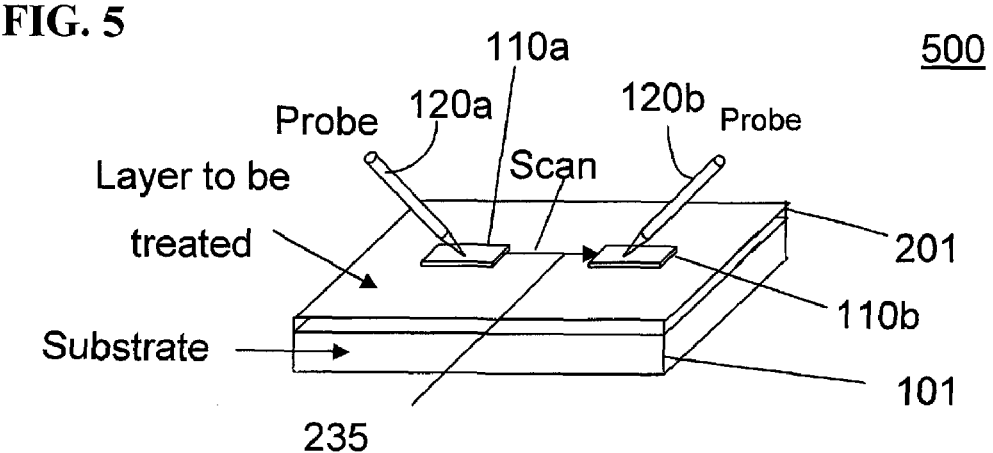
FIG. 5 illustrates an example of a method of direct fabrication, in accordance with an embodiment of the disclosure.

FIG. 5 illustrates one example of direct fabrication 500, in accordance with an embodiment of the disclosure. FIG. 5 is substantially similar to the configuration of FIG. 2A. For example, when laser beam 130 is scanned to achieve a process effect, such as, for example, to generate a conductive channel 235, contact electrodes 110a and 110b are contacted with probes 120a and 120b, respectively, to measure resistivity/conductivity as processing advances. Representative processes provided by light source 130 may include ablation, annealing, activation, crystalline re-growth, etc. At a desired endpoint, the processing may be terminated, as indicated by predetermined current or voltage values. In this case the light beam performs the processing function, and the electrical measurements support the process control. Alternatively, the light source may be used as a nondestructive probe to monitor processes that may be controlled by electrical bias applied to electrode pads 110 on substrate 101.

Figure 6A:
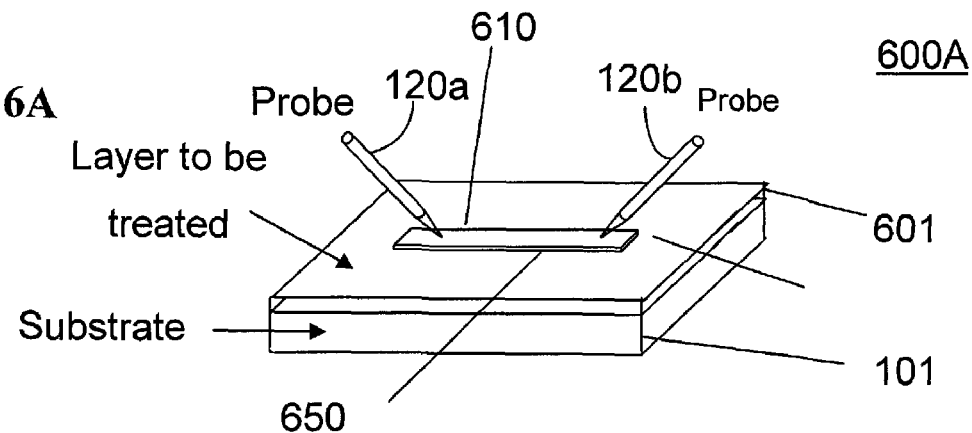
FIGS. 6A and 6B illustrate examples of a method of direct fabrication, in accordance with an embodiment of the disclosure.
Figure 6B:
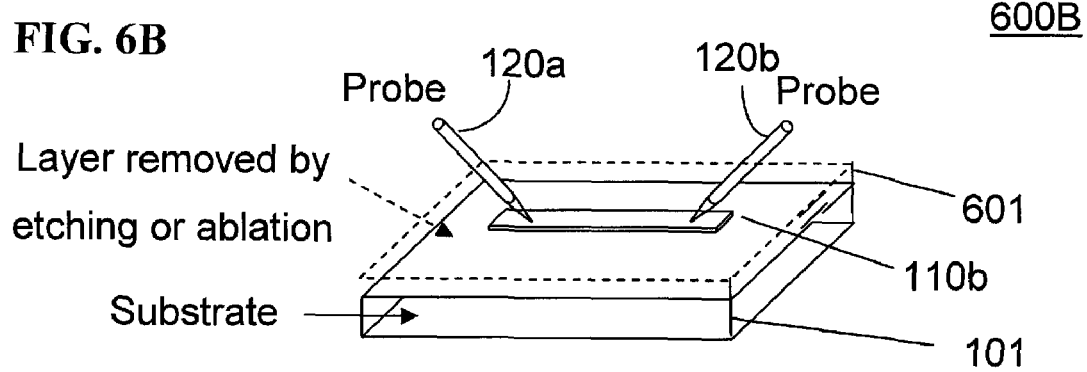

FIGS. 6A and 6B illustrate an example of direct fabrication, which may be implemented in a variety of ways. For example, referring to FIG. 6A, probes 120a and 120b contact substrate 101 in a test region 650 of layer 601, which is to be subjected to a process. Region 650 may be a conductive electrode, an insulator, or an ohmic contact, formed by a number of methods, or representative of the substrate prior to the process step. An additional probe (not shown) may make contact through the base of substrate 101. As substrate 101 is processed, for example, by ablation, ion implantation, annealing, etc., the resistivity measure between probes 120a and 120b may increase or decrease, depending on the process. Similarly, the resistivity measured by one or both probes 120a and 120b to the substrate may also change, and the change may not be uniform over the surface, depending on the nature of the process, such as scanned laser annealing, so that probes 120a and 120b may obtain different measurement values. In this case, suitable alterations in details (not shown) of circuit 200 of FIG. 2A would be made to facilitate these measurements. Alternatively, a voltage bias or current drive may be applied to region 650 using another suitable circuit (not shown) in conjunction with another process (e.g., thermal annealing or ion implantation), and a region of preferential properties may be formed in or under region 650 in layer 601.

FIG. 6B illustrates a variation of possible processes obtained as in FIG. 6A, where layer 601 is to be removed by etching or ablation. By control of voltages and/or currents applied between probes 120a and 120b, and/or substrate 101, removal of material in region 650 may be selectively enhanced or prevented.

Figure 7:
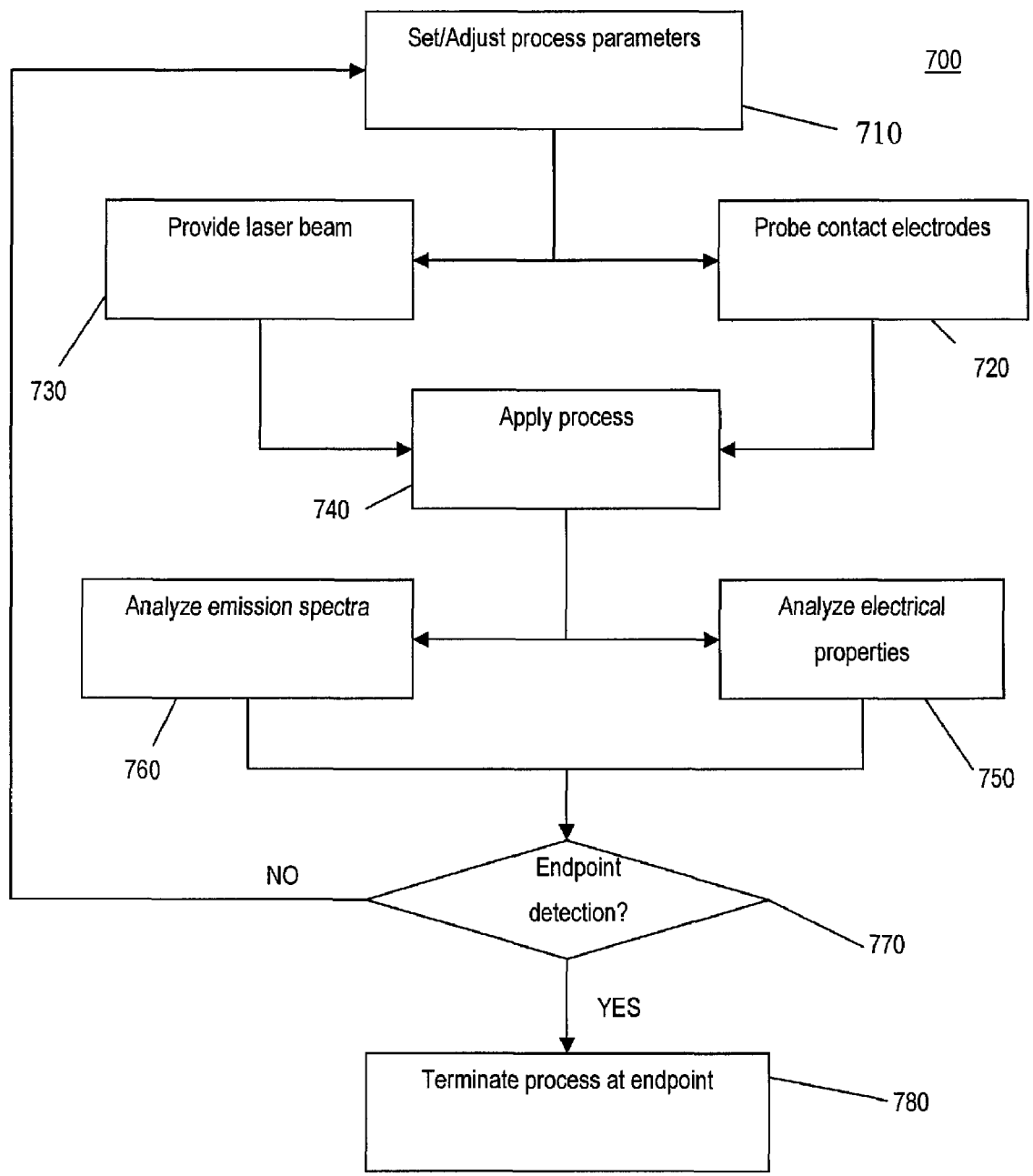
FIG. 7 is a diagram of a method of combined in situ process monitoring, optimization and fabrication according to one embodiment.

FIG. 7 is a diagram of a method 700 of combined in situ process monitoring, optimization and fabrication. Method 700 includes setting process parameters (block 710) with desired endpoint device performance objectives. Electrodes 110 on substrate 101 are contacted (block 720) using a plurality of probes 120 connected to a circuit for applying voltages and currents for processing, monitoring, control, and process optimization. Laser beam 130 is provided (block 730) to substrate 101 to perform processing and/or provide an optical source for monitoring, control and optimization. While all the possible configurations are not shown, the steps of block 720 (i.e., electrical processing and/or monitoring) and block 730 (i.e., optical processing and/or monitoring) may be performed simultaneously, alternatively, or sequentially, as needed by the requirements of a specific device fabrication on substrate 101.

Method 700 continues by applying the process (block 740), which may include process methods in addition to and different from optical and electrical process effects. Electrical property analysis (block 750) and optical emission spectra analysis (block 760) may take place individually or simultaneously to monitor the process and provide data for control and optimization of the ongoing fabrication process. According to the process parameters set in block 710, measured parameters are compared to process endpoint goals (block 770). If the process goal conditions are satisfied (i.e., YES), the process is terminated (780). If the process goals are not yet satisfied (i.e., NO), the method repeats at block 710 by adjusting the process operating conditions, until termination conditions (block 780) are successfully met.

FIGS. 8A-8C illustrate various methods for implementing process monitoring and control for fabrication optimization.

FIG. 8A illustrates an in situ method 8000, which essentially incorporates method 700 from FIG. 7 of a combined in situ process monitoring, optimization and fabrication. A first process (Process A) is provided or performed in a first station (Station 1) at block 8010. Station 1 may be a vacuum processing chamber or other workstation at which Process A is performed. Method 8000 proceeds substantially as described in method 700, with blocks 8010 TO 8050 in FIG. 8A corresponding substantially to blocks 710 TO 770. If an endpoint is not detected (No in block 8050) Process A is continuously performed in situ in the loop by returning to block 8010. If an endpoint is detected in block 8050 (i.e., Yes) Process A is terminated (corresponding to block 780 in FIG. 7, and processing continues with a second process (Process B) at a second station (Station B) at block 8160.

FIG. 8B illustrates an ex situ method 8200, in which a first process (Process A) performed in a first station (Station 1) has been completed (block 8210). The device or substrate in process is then transferred to a second station (Station 2) in block 8220, which may be a chamber or workstation adapted for process evaluation. Optical and/or electrical measurements are taken on the device or substrate at block 8230, as described above, to characterize the results of Process A. The optical and/or electrical measurements are then analyzed at block 8240, for example, optical spectra and electrical properties of devices, components and selected regions of a substrate. The analysis provided in block 8240 is used to determine whether Process A yielded passing results in block 8250. If the results are satisfactory (i.e., a "Pass"), the substrate or device is transferred to a third station (Station 3) for additional processing (Process B) in block 8260. If the results are not satisfactory (i.e., not a "Pass"), the substrate may, for example, be returned to Station 1 for continued processing by Process A, or the operational parameters of Process A (block 8210) in Station 1 may be modified for subsequent substrates so that Process A would more likely yield passing results.

FIG. 8C illustrates an inline method 8300, in which Process A performed in Station 1 (block 8310) is first completed. Properties of the substrate or device are then measured to determine whether Process A yielded passing results in blocks 8320, 8330, and 8340, which are substantially identical with blocks 8230, 8240, and 8250 of FIG. 8B. If the results are satisfactory (i.e., a "Pass"), a second process (Process B) is performed on the substrate or device (in block 8350). Process B may take place in the same station (Station 1) or may be performed in a different station (Station 2). If Process B is performed in Station 2, the device or substrate is transferred to Station 2, where Station 2 may also be equipped to measure the results of Process B on the device or substrate. If results of a process are not satisfactory (i.e., not a "Pass"), the substrate or device may, for example, be returned to Station 1 (or any other station which performed the unsatisfactory processing) for continued processing. The operational parameters of the process may be modified for the current or subsequent substrates as determined by the measurements. Thus, it may be understood that inline process monitoring and optimization may be implemented in various ways.

In addition, as mentioned with respect to the above listed processes and obvious variations, process optimization and control may be achieved by controlling endpoint termination of the process.

Also, only those claims which use the word "means" are intended to be interpreted under 35 USC 112, sixth paragraph. Moreover, no limitations from the specification are intended to be read into any claims, unless those limitations are expressly included in the claims. Accordingly, other embodiments are within the scope of the following claims.

What is claimed is:

1. A method of monitoring the processing of semiconductor materials and devices comprising:
   providing electrical contact pads on a substrate;
   directing a light beam of a selected wavelength and a selected power onto the substrate;
   applying electrical voltages and/or currents between a plurality of the contact pads and/or the substrate to perform one or more process steps while applying the light beam;
   optically measuring properties from the light produced at the substrate by the light beam while applying the electrical voltages and/or currents;
   measuring at least one electrical property between a plurality of the contact pads and/or the substrate while applying the light beam; and
   controlling at least one process step on the basis of the electrical and optical measurements.

2. The method of claim 1, wherein the light beam is a laser beam or an incoherent light source.

3. The method of claim 1, wherein the light beam is a continuous, pulsed or modulated beam.

4. The method of claim 1, wherein the providing electrical contact pads comprises fabricating with one or more deposited conductive layers, semiconductors or insulators and patterned with photolithography or through a mask.

5. The method of claim 1, wherein the providing electrical contact pads comprises fabricating by selectively scanning the substrate with the light source to anneal the substrate, activate implanted ions, or initiate a reaction at the surface in the presence of chemical vapors to deposit suitable materials.

6. The method of claim 1, wherein the measuring the electrical properties comprises applying voltages and/or currents to the electrical contact pads to measure resistance.

7. The method of claim 1, wherein the optically measuring comprises one or more of refraction, reflection, diffraction, scattering, optical emission spectroscopy, Raman spectroscopy and ellipsometry.

8. The method of claim 1, wherein the controlling comprises changing the voltage and/or current operating parameters according to the measured optical and electrical properties.

9. The method of claim 1, wherein the controlling comprises changing the light beam wavelength, directing, and/or power according to the measured optical and electrical properties.

10. The method of claim 1, wherein the directing, measuring, and/or controlling at least one process step is in situ.

11. The method of claim 1, wherein the directing, measuring, and/or controlling at least one process step is ex situ.

12. The method of claim 1, wherein the directing, measuring, and/or controlling at least one process step is inline.

* * * * *